(12) United States Patent
Pye et al.

(10) Patent No.: US 12,215,110 B2
(45) Date of Patent: Feb. 4, 2025

(54) PROCESSES AND INTERMEDIATES FOR PREPARING A BTK INHIBITOR

(71) Applicant: JANSSEN PHARMACEUTICA NV, Beerse (BE)

(72) Inventors: Philip James Pye, Bridgewater, NJ (US); Andras Horvath, Turnhout (BE); Cheng Yi Chen, San Diego, CA (US); Yuanyuan Yuan, Changzhou (CN); Jinxiong Su, Changzhou (CN); Shuo Wang, Changzhou (CN); Simon Albert Wagschal, Schaffhausen (CH)

(73) Assignee: Janssen Pharmaceutica NV, Beerse (BE)

( * ) Notice: Subject to any disclaimer, the term of this patent is extended or adjusted under 35 U.S.C. 154(b) by 681 days.

(21) Appl. No.: 17/612,082

(22) PCT Filed: May 20, 2020

(86) PCT No.: PCT/EP2020/064123
§ 371 (c)(1),
(2) Date: Nov. 17, 2021

(87) PCT Pub. No.: WO2020/234381
PCT Pub. Date: Nov. 26, 2020

(65) Prior Publication Data
US 2022/0204516 A1      Jun. 30, 2022

(30) Foreign Application Priority Data

May 21, 2019   (WO) ................ PCT/CN2019/087823

(51) Int. Cl.
*C07D 487/04*   (2006.01)

(52) U.S. Cl.
CPC .................................. *C07D 487/04* (2013.01)

(58) Field of Classification Search
CPC .................................................. C07D 487/04
See application file for complete search history.

(56) References Cited

U.S. PATENT DOCUMENTS

| 9,409,911 B2 | 8/2016 | Honigberg et al. | |
|---|---|---|---|
| 2011/0082137 A1* | 4/2011 | Giovannini | A61P 25/00 544/118 |
| 2014/0275126 A1 | 9/2014 | Pye et al. | |
| 2015/0111887 A1 | 4/2015 | Hodous et al. | |
| 2018/0009814 A1 | 1/2018 | Benhaim et al. | |
| 2018/0044339 A1 | 2/2018 | Zhang et al. | |
| 2022/0098200 A1 | 3/2022 | Ben et al. | |

FOREIGN PATENT DOCUMENTS

| CN | 103121999 A | 5/2013 |
|---|---|---|
| JP | 2016-538257 A | 12/2016 |
| JP | 2018-502077 A | 1/2018 |
| JP | 2018-513205 A | 5/2018 |
| WO | 2008/039218 A2 | 4/2008 |
| WO | 2014/139970 A1 | 9/2014 |
| WO | 2016/115356 A1 | 7/2016 |

OTHER PUBLICATIONS

Chen, C-Y., et al., "A Copper-Catalyzed Tandem C—H ortho-Hydroxylation and N—N Bond-Formation Transformation: Expedited Synthesis of 1-(ortho-Hydroxyaryl)-1H-indazoles," European Journal of Organic Chemistry, vol. 2017, Issue 45, Dec. 8, 2017, pp. 6604-6608.

Chen, C-Y., et al., "A Synthesis of 1H-Indazoles via a Cu(OAc)2-Catalyzed N—N Bond Formation," Organic Letters, vol. 18, No. 7, pp. 1690-1693.

Horwood N. J. et al., "Bruton's Tyrosine Kinase Is Required for Lipopolysaccharide-induced Tumor Necrosis Factor α Production," The Journal of Experimental Medicine, vol. 197, Issue 12, 2003, pp. 1603-1611.

Iwaki et al, "Btk Plays a Crucial Role in the Amplification of Fc?RI-mediated Mast Cell Activation by Kit," Journal of Biological Chemistry, vol. 280, Issue 48, 2005, pp. 40261-40270.

Jefferies C. A. et al, "Bruton's Tyrosine Kinase Is a Toll/Interleukin-1 Receptor Domain-binding Protein That Participates in Nuclear Factor B Activation by Toll-like Receptor 4," Journal of Biological Chemistry, vol. 278, Issue 28, 2003, pp. 26258-26264.

Kosobokov, M.D., et al., "Nitrogen-Nitrogen Bond Formation via a Substrate-Bound Anion at a Mononuclear Nickel Platform," Organometallics, vol. 37, No. 4, Feb. 5, 2018, pp. 521-525.

(Continued)

*Primary Examiner* — Timothy R Rozof
(74) *Attorney, Agent, or Firm* — BakerHostetler

(57) ABSTRACT

Disclosed is a process for the preparation of certain intermediates, e.g. a process for preparing a compound of formula (I) wherein, $R^1$, $R^2$ and $X^1$ are as defined in the description, and which intermediate and processes are useful in the preparation of a BTK inhibitor, such as ibrutinib.

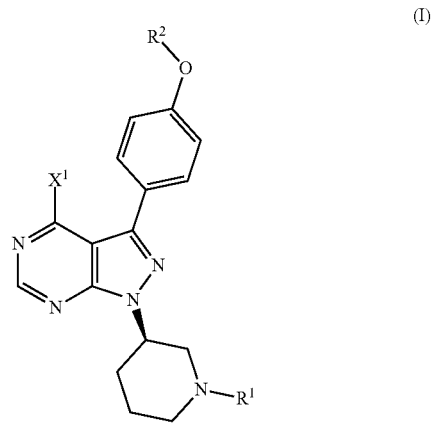

(I)

22 Claims, No Drawings

(56) References Cited

OTHER PUBLICATIONS

Kurosaki, "Functional dissection of BCR signaling pathways," Current Opinion in Immunology, vol. 12, Issue 3, Jun. 1, 2000, pp. 276-281.

Quek et al, "A role for Bruton's tyrosine kinase (Btk) in platelet activation by collagen," Current Biology, vol. 8, Issue 20, 1998, pp. 1137-1140.

Schaeffer E.M. et al, "Tec family kinases in lymphocyte signaling and function," Current Opinion in Immunology, vol. 12, Issue 3, Jun. 1, 2000, pp. 282-288.

Vassilev et al, "Bruton's Tyrosine Kinase as an Inhibitor of the Fas/CD95 Death-inducing Signaling Complex," Journal of Biological Chemistry, vol. 274, Issue 3, 1999, pp. 1646-1656.

\* cited by examiner

PROCESSES AND INTERMEDIATES FOR PREPARING A BTK INHIBITOR

CROSS-REFERENCE TO RELATED APPLICATIONS

This application is the National Stage of International Patent Application No. PCT/EP2020/064123, filed May 20, 2020, which claims the benefit of International Patent Application No. PCT/CN2019/087823, filed May 21, 2019, the disclosures of which are incorporated herein by reference in their entireties.

FIELD OF THE INVENTION

The present invention relates to synthesis procedures and synthesis intermediates of substituted bicyclic compounds, especially compounds that are useful as medicaments, for instance Bruton's tyrosine kinase (Btk) inhibitors such as ibrutinib.

BACKGROUND OF THE INVENTION

Ibrutinib is an organic small molecule having IUPAC name 1-[(3R)-3-[4-amino-3-(4-phenoxyphenyl)pyrazolo[3,4-d]pyrimidin-1-yl]piperidin-1-yl]prop-2-en-1-one. It is described in a number of published documents, including international patent application WO 2008/039218 (Example 1b), and is described as an irreversible inhibitor of Btk.

Btk plays an essential role in the B-cell signaling pathway linking cell surface B-cell receptor stimulation to downstream intracellular responses. Btk is a key regulator of B-call development, activation, signaling, and survival (Kurosaki, *Curr Op Imm*, 2000, 276-281; Schaeffer and Schwartzberg, *Curr Op Imm* 2000, 282-288). In addition, Btk plays a role in a number of other hematopoetic cell signaling pathways, e.g. Toll like receptor (TLR) and cytokine receptor-mediated TNF-α production in macrophages, IgE receptor (FcepsilonRI) signaling in Mast cells, inhibition of Fas/APO-1 apoptotic signaling in B-lineage lymphoid cells, and collagen-stimulated platelet aggregation. See e.g., C. A. Jeffries, et al., (2003), *Journal of Biological Chemistry* 278:26258-26264; N. J. Horwood, et al., (2003), *The Journal of Experimental Medicine* 197:1603-1611; Iwaki et al. (2005), *Journal of Biological Chemistry* 280 (48):40261-40270; Vassilev et al. (1999), *Journal of Biological Chemistry* 274(3):1646-1656, and Quek et al (1998), *Current Biology* 8(20):1137-1140.

Ibrutinib has been approved for certain hematological malignancies in several countries including the US and the EU, and is also being studied in clinical trials for other hematological malignancies. Such malignancies include chronic lymphocytic leukemia, mantle cell lymphoma, diffuse large B-cell lymphoma and multiple myeloma.

There are a number of ways of preparing functionalised bicyclic heterocycles and ibrutinib, which have been described in inter alia US patent document US 2011/0082137 and international patent application WO 2008/039218 (Example 1b). In relation to the latter, the latter steps for synthesising ibrutinib are shown in the following scheme:

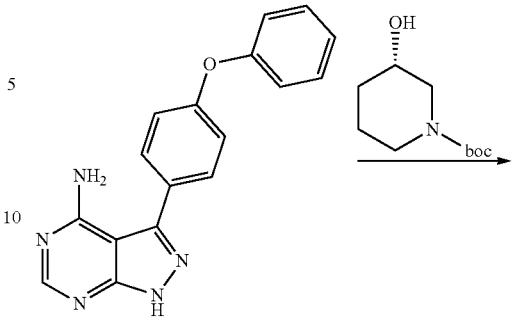

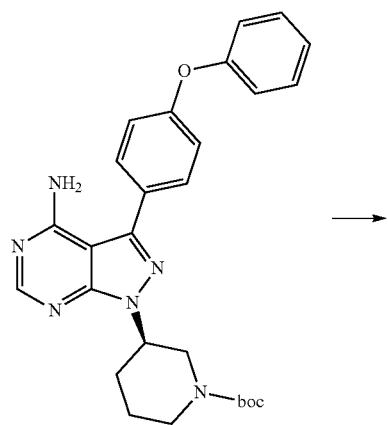

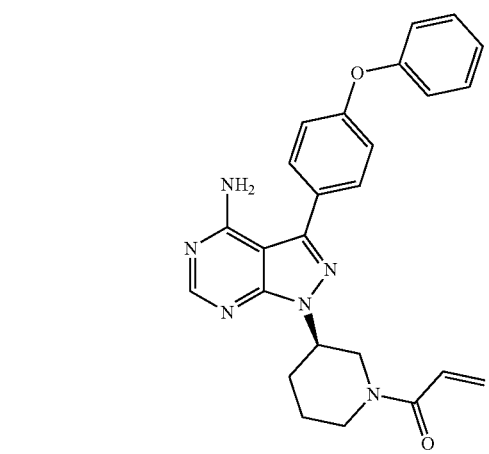

It can be seen that the core heterobicyclic part of ibrutinib, i.e. the pyrazolopyrimidine is already built up before the introduction of the chiral piperidinyl moiety. The bicyclic ring itself is built up by preparing a pyrazole intermediate substituted at the 3- and 4-position by an amino and cyano group, respectively, followed by reaction with formamide.

Other methods for synthesising ibrutinib have been disclosed in international patent application WO 2014/139970, including through the following scheme:

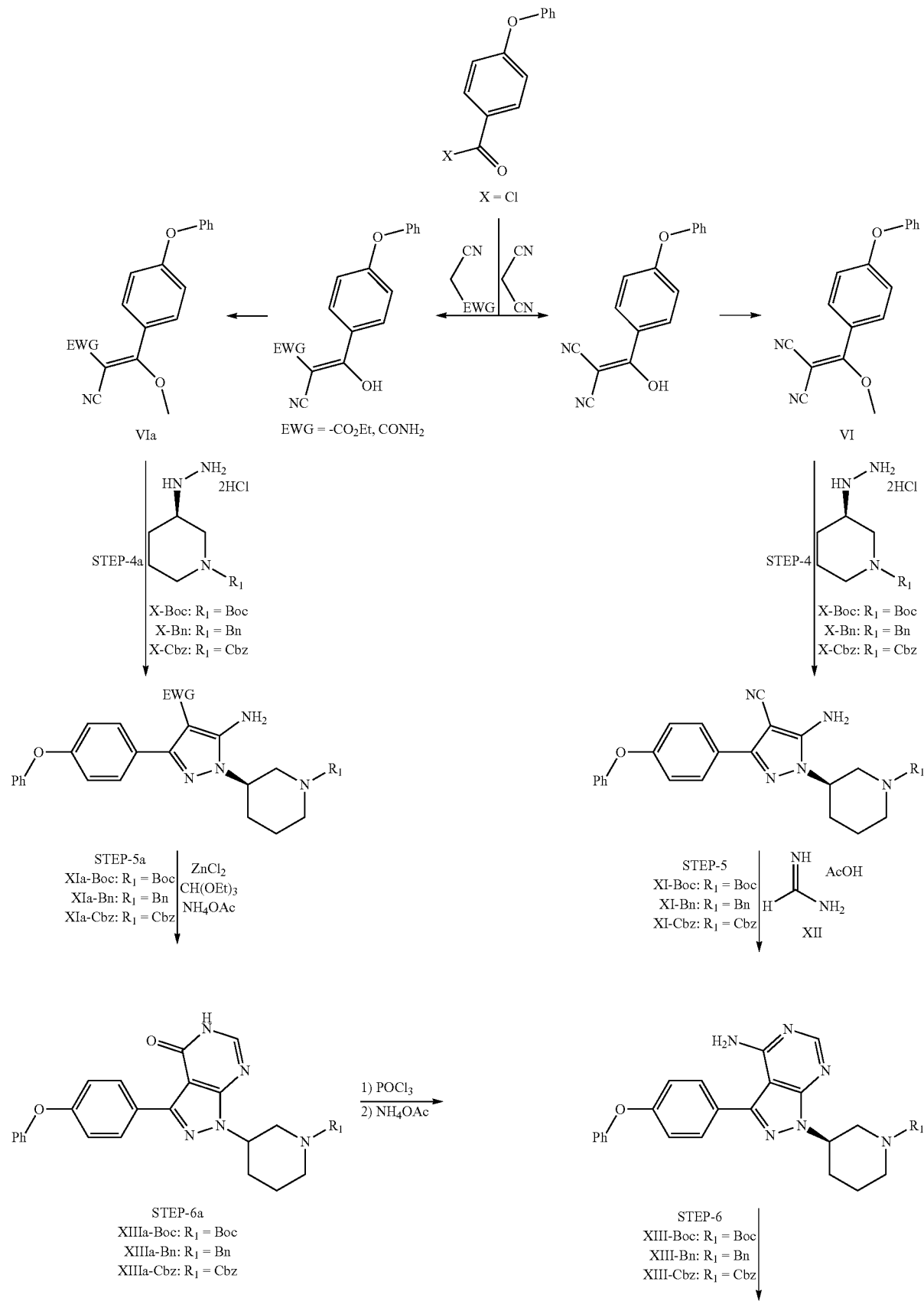

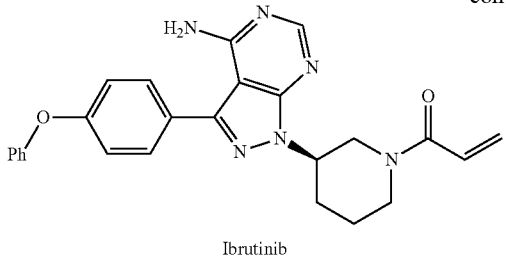

Ibrutinib

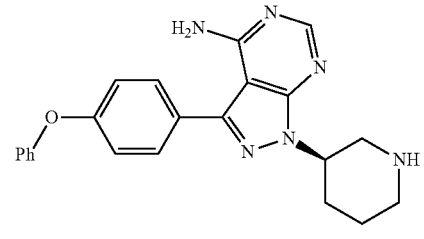

I

-continued

In this case, the core heterobicycle of ibrutinib, i.e. the pyrazolopyrimine is built up through an intermediate having a pyrazole ring substituted at the 3- and 4-positions with an amino and cyano group, respectively. From this intermediate, the pyrimidine part of the core heterobicycle pyrazolpyrimidine can also be built up, and then further functionalised to form ibrutinib.

The final step to introduce the substituent on the nitrogen atom of the piperidinyl ring may be performed in accordance with the above scheme and may also be performed with procedures described in international patent application WO 2016/115356, by reaction with 3-chloropropionyl chloride (for instance in the presence of aqueous $NaHCO_3$ in Me-THF), thereby introducing a —C(O)—$CH_2CH_2$—Cl group at the nitrogen atom of the piperidinyl. Such intermediate then undergoes an elimination reaction in the presence of DBU (1,8-diazabicyclo(5.4.0)undec-7-ene) to provide ibrutinib.

The above publications do not disclose alternative methods to synthesise the key core pyrazolopyrimidine heterobicycle. It is furthermore a challenge to synthesise a N—N bond (i.e. two nitrogen atoms together) within the context of a cycle. In this respect, the formation of an indazole has been described in journal article by Chen et al, Organic Letters, 2016, 18, 1690-1693 in a paper entitled "A synthesis of 1H-indazoles via a $Cu(OAc)_2$-catalysed N—N bond formation". However, this article does not disclose any synthesis of a pyrazolopyrimidine heterobicyclic core.

DESCRIPTION OF THE INVENTION

There is now provided a process for preparing a compound of formula (I)

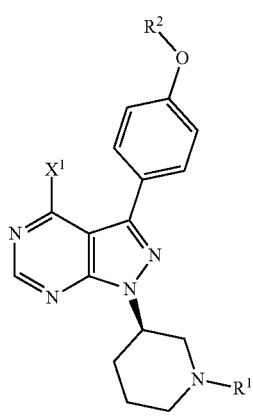

(I)

wherein
$R^1$ represents a nitrogen protecting group;
$R^2$ represents hydrogen or aryl (e.g. phenyl);
$X^1$ represents a substituent selected from a leaving group (e.g. halo, —O—$Y^1$, and the like) and —N($R^3$)$R^4$;
$Y^1$ represents hydrogen or a sulfone (e.g. —S(O)$_2$—$R^x$, in which $R^x$ may represent $C_{1-3}$ alkyl optionally substituted by one or more fluoro atoms, or, aryl (e.g. phenyl) optionally substituted by one or more substituents selected from halo and $C_{1-3}$ alkyl, which latter group may itself be optionally substituted by one or more fluoro atoms) and hence when $X^1$ represents —O—$Y^1$ a sulfonate group may be formed, e.g. $X^1$ may represent a tosylate, mesylate or triflate;
at least one of $R^3$ and $R^4$ represents a nitrogen protecting group, and the other represents hydrogen, or an independent nitrogen protecting group;
which process comprises reaction of a compound of formula (II)

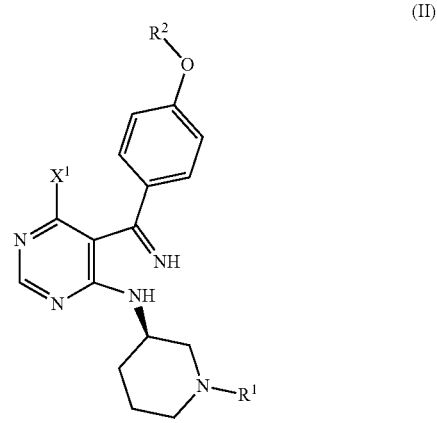

(II)

wherein $R^1$, $R^2$ and $X^1$ are as hereinbefore defined, in the presence of an oxidant (e.g. a source of oxygen, for instance air and, specifically, $O_2$ in the air) and a copper-based catalyst,
which process may be referred to herein as a process of the invention (which consists of one or more embodiments).

Herein, it is indicated in the process of the invention (and embodiments described herein) that a salt of the compound may be employed and/or produced. Alternatively (and in a preferred embodiment), the free base of the compound may be employed and/or produced. Further, if a salt form is employed and/or produced, it may be liberated to form the free base form (e.g. for further reaction, for instance for use in the further process steps such as those described herein).

It should also be noted that compounds mentioned herein may exhibit isomerism, e.g. tautomerism.

For the avoidance of doubt, the compound of formula (I) (and precursors) as well as downstream products are those in which the chiral centre denoted by * in the representative examples below is in the (R) configuration:

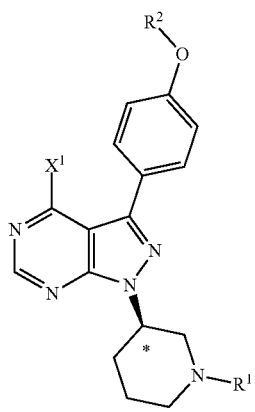

(I)

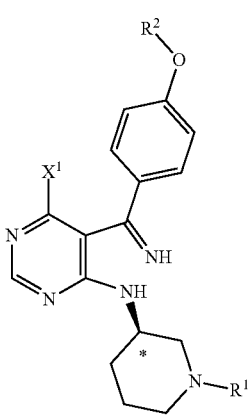

(II)

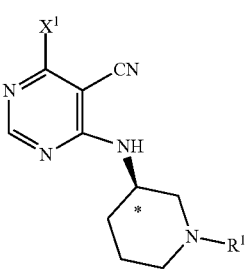

(III)

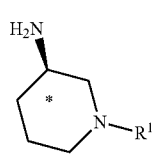

(VI)

Where we indicate that there is a compound (e.g. of formula (I), formula (II), formula (III), etc) in which there is an atom in the (R)-configuration, we mean that the (R)-enantiomer is the predominant enantiomer, and the compound has an ee of greater than 20% (and in embodiments in an ee greater still). For instance, the enantioenriched compounds (e.g. the compound of formula (I), formula (II), formula (III), etc) may be in an enantiomeric excess of greater than 40%, such as more than 60% and, in an embodiment, greater than 80% enantiomeric excess. The enantioenriched compounds may even be greater than 90% (for example, they may consist essentially of a single enantiomer, by which we mean that the ee may be 95% or higher, e.g. above 98% or about 100%). Such enantioenrichment (or ees) may be obtained directly, or through further purification techniques that are known to those skilled in the art.

For instance, the processes of several embodiments of the invention produce products that are enantioenriched. As an example, the compound of formula (V) that is employed in the processes of the invention described herein (in the reaction with a compound of formula (IV) to produce a compound of formula (III)) is enantioenriched, i.e. of an ee described herein (e.g. greater than 80% ee, etc). As enantiospecificity is introduced into the processes, downstream reactions/process steps may be stereospecific, that is the stereochemistry is retained in the downstream products, i.e. the ee of the compound of formula (III) is linked to the ee of the precursor compound of formula (V) from which it is obtained. Likewise, the ee of the compound of formula (I) is linked to the ee of the compound of formula (III) from which it is obtained (and so on). Downstream process steps may also be stereospecific and retain such stereochemistry, which is an advantage for producing final medicinal products that are single enantiomers such as ibrutinib. The fact that the enantioselectivity is introduced early in the reaction scheme is an advantage in terms of efficiency as less product is wasted.

In the process of the invention described herein, a new N—N bond is formed in the preparation of a compound of formula (I). In order to achieve this, in an embodiment (a) suitable copper-based catalyst(s) is employed. Such reaction is performed in the presence of an oxidant, such as $O_2$ in the air. Suitable catalysts that may be employed include $Cu(OAc)_2$, CuBr and other copper halides in which the halide may be fluoro, iodo, bromo and chloro, in particular chloro and bromo (especially chloro). It may be the case that compounds of formula (II) in which $X^1$ represents halo (e.g. chloro) are converted to compounds of formula (I) in which $X^1$ represents —OH in the presence of a certain copper catalyst (e.g. $Cu(OAc)_2$), whereas in the presence of other copper catalysts (e.g. copper halide), the identity of the $X^1$ moiety may be preserved.

The compound of formula (II) may be prepared by reaction of a compound of formula of formula (III)

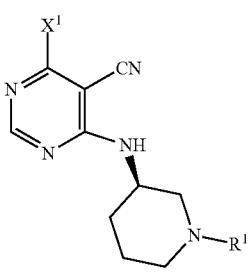

(III)

or a salt thereof, wherein $R^1$ and $X^1$ are as hereinbefore defined, with a compound of formula (IV),

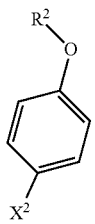

(IV)

or a salt thereof, wherein $R^2$ is as defined, and $X^2$ represents a halo group [in the presence of an organometallic, especially an organolithium base; in this case the lithium can exchange with the halo group (at $X^2$) so forming a nucleophile that forms a bond with the carbon atom of the cyano moiety of the compound of formula (III) ultimately forming the imine moiety of the desired compound of formula (II). The reaction, and the key part of forming the organolithium, may be performed in the presence of a suitable solvent, such as a polar aprotic solvent e.g. THF.

The compound of formula (III) may be prepared by reaction of a compound of formula (V),

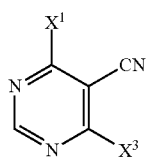

(V)

or a salt thereof, wherein $X^1$ is as hereinbefore defined, and $X^3$ represents a suitable leaving group such as halo (e.g. chloro, bromo or iodo) or —O—$Y^2$, and $Y^2$ represents a sulfone (e.g. —S(O)$_2$—$R^y$, in which $R^y$ may represent $C_{1-3}$ alkyl optionally substituted by one or more fluoro atoms, or, aryl (e.g. phenyl) optionally substituted by one or more substituents selected from halo and $C_{1-3}$ alkyl, which latter group may itself be optionally substituted by one or more fluoro atoms) and hence $X^3$ may form a sulfonate, for instance a tosylate, mesylate or triflate, with a compound of formula (VI)

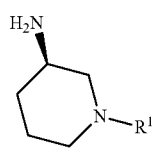

(VI)

or a salt thereof, wherein $R^1$ is as hereinbefore defined, under nucleophilic aromatic substitution reaction conditions; for such reaction to successfully proceed, the $X^3$ group acts as a good leaving group, and the ortho-cyano substituent acts as a suitable electron-withdrawing moiety to facilitate the nucleophilic substitution. This reaction may be performed in the presence of a suitable base such as a carbonate base, e.g. an alkali metal carbonate, $Na_2CO_3$ or the like.

Compounds of formula (VI) may be prepared by resolution. In a further embodiment of the invention, the following process/method may be employed.

Certain starting materials and certain intermediates may also be either commercially available or may be prepared according to conventional reaction procedures generally known in the art.

All individual features (e.g. preferred features) mentioned herein may be taken in isolation or in combination with any other feature (including preferred feature) mentioned herein (hence, preferred features may be taken in conjunction with other preferred features, or independently of them).

The skilled person will appreciate that compounds mentioned in the context of the process of the invention are those that are stable. That is, compounds included herein are those that are sufficiently robust to survive isolation from e.g. a reaction mixture to a useful degree of purity.

In an embodiment of the invention, the following compounds of formula (I) are provided in the process of the invention, those in which:
$X^1$ represents halo (e.g. chloro) or —O—$Y^1$; and/or
$Y^1$ represents hydrogen.

In a further embodiment of the invention, the following compounds of formula (I) are provided in the process of the invention, those in which:
$R^2$ represents phenyl (unsubstituted; so forming the appropriate substituent that is contained in ibrutinib).

It is stated herein that compounds of formula (I) prepared by the processes described herein are those in which $R^1$ represents a nitrogen protecting group. In this respect, it will be understood that the following protecting groups are included, i.e. those that result in the formation of:
an amide (e.g. N-acetyl)
optionally substituted N-alkyl (e.g. N-allyl or optionally substituted N-benzyl)
N-sulfonyl (e.g. optionally substituted N-benzenesulfonyl)
a carbamate
a urea
trityl (triphenylmethyl), diphenylmethyl, or the like
Hence, $R^1$ may represent:
—C(O)$R^{r1}$ (in which $R^{r1}$ may represent $C_{1-6}$ alkyl or optionally substituted aryl); $C_{1-6}$ alkyl, which alkyl group is optionally substituted by one or more substituents selected from optionally substituted aryl (e.g. may form a benzyl moiety); —S(O)$_2R^{r2}$ (in which $R^{r2}$ may represent optionally substituted aryl); or, in an embodiment, —C(O)O$R^{r3}$ (in which $R^{r3}$ may represent optionally substituted aryl or, in a further embodiment, optionally substituted $C_{1-6}$ (e.g. $C_{1-4}$) alkyl, e.g. tert-butyl (so forming, for example, a tert-butoxycarbonyl protecting group, i.e. when taken together with the amino moiety, a tert-butylcarbamate group) or a —CH$_2$phenyl group (so forming a carboxybenzyl protecting group));
—C(O)N($R^{r4}$)$R^{r5}$ (in which, in an embodiment, $R^{r4}$ and $R^{r5}$s independently represent hydrogen, $C_{1-6}$ alkyl, optionally substituted aryl or —C(O)$R^{r6}$, and $R^{r6}$ represents $C_{1-6}$ alkyl or optionally substituted aryl).

In an embodiment, $R^1$ represents —C(O)O$R^{r3}$ (in which $R^{r3}$ may represent $C_{1-6}$ alkyl, e.g. tert-butyl) and, hence, in an aspect, the $R^1$ protecting group is tert-butoxycarbonyl (also known as, and referred to herein, as a BOC or Boc group).

However, the choice of protecting group that $R^1$ may represent in the processes described herein is flexible. Furthermore, one $R^1$ protecting group may be converted to another in any of the compounds described herein, for instance when it is advantageous for a certain protecting group to be employed in a certain process step (and a different protecting group to be employed in a subsequent or preceding process step).

Compounds of formula (II) that may be employed in the process of the invention (e.g. to provide compounds of formula (I) in which $X^1$ represents halo (e.g. chloro) or —O—$Y^1$), include those in which $X^1$ represent halo (e.g. chloro). In particular, compounds of formula (II) in which $X^1$ represents halo (e.g. chloro) are converted (in accordance with the procedures described herein) to compounds of formula (I) in which $X^1$ represents halo (e.g. chloro) or —OH (i.e. —$OY^1$ in which $Y^1$ represents hydrogen).

In a further embodiment, certain compounds of formula (I) may be converted into other compounds of formula (I), depending on the desired downstream product to be synthesised. For example, in such instances where, in the processes described herein, a compound of formula (I) in which $X^1$ represents —OH is provided, it may be desired to convert such an $X^1$ group into a better leaving group, for instance a group in which $X^1$ represents —$OY^1$ and $Y^1$ represents a sulfone as hereinbefore defined (i.e. —$S(O)_2$—$R^x$, where $R^x$ is as hereinbefore defined). Such a conversion may be useful in providing further downstream products, e.g. to introduce other (more diverse array of) substituents at the $X^1$ position (e.g. through a nucleophilic aromatic substitution reaction). Such compounds of formula (I) in which $X^1$ represents —$OY^1$ in which $Y^1$ represents —$S(O)_2$—$R^x$ may be prepared from corresponding compounds in which $X^1$ represents —OH with a compound of formula LG-$S(O)_2$—$R^x$ (in which $R^x$ is as hereinbefore defined, and LG represents a suitable leaving group such as halo, but may also represent a —$OS(O)_2$—$R^x$ group, where $R^x$ is as herein defined, and the two $R^x$ groups may be the same or different, but are preferably the same). Such reactions may take place in the presence of a base and optionally a suitable solvent (e.g. they may take place in the presence of pyridine). As an example, compounds of formula (I) in which $X^1$ represents —OH may be reacted with trifluoromethanesulfonic acid anhydride, i.e. $(CF_3SO_2)_2O$ or $F_3C$—$S(O)_2$—O—$S(O)_2CF_3$, e.g. in the presence of pyridine, so forming a triflate leaving group; in a similar manner other leaving groups such as mesylate and tosylate may also be formed.

Compounds of formula (I) in which $R^2$ represents aryl (e.g. phenyl) may be prepared from corresponding compounds of formula (I) in which $R^2$ represents hydrogen, for instance by reaction of a compound of the following formula $R^{2a}$-$L^{xa}$ (where $R^{2a}$ represents aryl, e.g. phenyl, and $L^{xa}$ represents a suitable leaving or coupling group such as —$B(OH)_2$, —$B(OR^w)_2$ or —$Sn(R^w)_3$, in which each $R^w$ independently represents a $C_{1-6}$ alkyl group, or, in the case of —$B(OR^w)_2$, the respective $R^w$ groups may be linked together to form a 4- to 6-membered cyclic group (such as a 4,4,5,5-tetramethyl-1,3,2-dioxaborolan-2-yl group, thereby forming e.g. a pinacolato boronate group) and where such a group may be prepared from a corresponding compound with a halo atom), and such a reaction may be performed in the presence of a suitable catalyst system, e.g. a metal (or a salt or complex thereof) such as Pd, CuI, Pd/C, $Pd(OAc)_2$, $Pd(Ph_3P)_2Cl_2$, $Pd(Ph_3P)_4$, $Pd_2(dba)_3$ and/or $NiCl_2$ (preferred catalysts include palladium) and a ligand such as $PdCl_2(dppf)$.DCM, t-$Bu_3P$ or the like, optionally in the presence of a suitable base (e.g. a carbonate base, hydroxide base, etc) and a suitable solvent.

Compounds of formula (I) (for instance those in which $X^1$ represents a "leaving group" such as halo (e.g. chloro) or a —$OY^1$ group in which $Y^1$ represents —$S(O)_2$—$R^x$ may then be converted to other compounds of formula (I) in which $X^1$ represents —$N(R^3)R^4$ (in which $R^3$ and $R^4$ are as hereinbefore defined). Such compounds may be converted, for instance by reaction of such a compound of formula (I) (in which $X^1$ represents a relevant "leaving group") with the following compound of formula $HN(R^3)R^4$, wherein $R^3$ and $R^4$ are as hereinbefore defined (and preferably both represent hydrogen, or at least one represents hydrogen and the other represents hydrogen or a nitrogen protecting group as hereinbefore defined. Protecting groups that may be mentioned include those hereinbefore defined, and in an embodiment may represent benzyl or PMB (4-methoxy-benzyl). If desired such protecting groups may be removed using methods described herein/known to those skilled in the art.

In an embodiment, compounds prepared in accordance with the procedures described (for instance, compounds of formula (I) in which $X^1$ represents —$NH_2$, $R^2$ represents unsubstituted phenyl, and $R^1$ represents hydrogen or a nitrogen protecting group—in which case the nitrogen protecting group may be removed in accordance with the descriptions herein) may then be employed to prepare ibruintib. For example under conditions described in either WO 2014/139970 or WO 2016/115356; for instance such compound may be reacted with Cl—C(O)—C(H)=$CH_2$ or a two-step process may be performed by reaction with 3-chloropropionyl chloride (for instance in the presence of aqueous $NaHCO_3$ in Me-THF), thereby forming a compound of formula (VII),

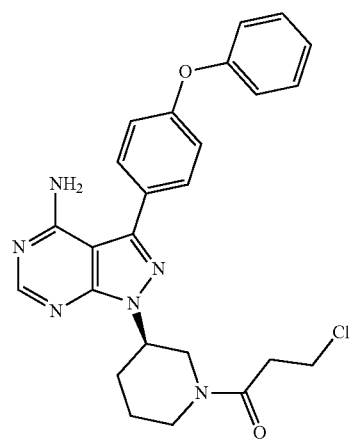

VII or a derivative thereof, wherein such intermediate may undergo an elimination reaction e.g. in the presence of DBU (1,8-diazabicyclo(5.4.0)undec-7-ene) to provide ibrutinib.

For the avoidance of doubt, the formula of ibrutinib (which is prepared in an embodiment of the invention) is as follows:

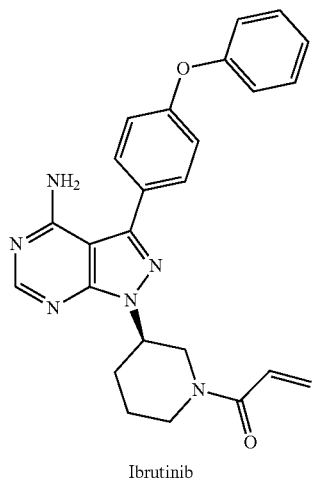 [SMILES: C=CC(=O)N1CCC[C@@H](n2nc(-c3ccc(Oc4ccccc4)cc3)c3c(N)ncnc32)C1]

Ibrutinib

Unless otherwise specified, alkyl groups as defined herein may be straight-chain or, when there is a sufficient number (i.e. a minimum of three) of carbon atoms be branched-chain, and/or cyclic. Further, when there is a sufficient number (i.e. a minimum of four) of carbon atoms, such alkyl groups may also be part cyclic/acyclic. Such alkyl groups may also be saturated or, when there is a sufficient number (i.e. a minimum of two) of carbon atoms, be unsaturated (including therefore e.g. "vinyl" moieties).

The process of the invention produces enantioenriched forms or products, by which we mean the products produced have an enantiomeric excess of greater than 20%, for instance greater than 40%, such as more than 60% and, in an embodiment, greater than 80% enantiomeric excess. The enantioenriched products may even be greater than 90% (for example, they may consist essentially of a single enantiomer, by which we mean that the ee may be 95% or higher, e.g. above 98% or about 100%). Such enantioenrichment (or ees) may be obtained directly, or through further purification techniques that are known to those skilled in the art.

Where equivalents are referred to, for the avoidance of doubt, this is intended to mean molar equivalents.

In a further aspect of the invention, there is provided a process for separating the product obtained (compound of formula (I)) from the process of the invention (which may be referred to herein as the "compound of the invention"). The compound of the invention (or product obtained by the process of the invention) may thus be separated/isolated. This may be achieved in several ways:
flash column chromatography
precipitation/crystallisation
derivatisation, optionally followed by precipitation/crystallisation
extraction (e.g. derivatisation followed by extraction)
distillation In further embodiments of the invention, there is provided a process of the invention as described herein, following by yet further process steps.

The compound of formula (I) (in enantioenriched form) may be used in the preparation of further compounds, for example further pharmaceutical products (or intermediates thereto) such as pharmaceutical products that are useful in the treatment of cancer (such as hematological malignancies), and particularly the pharmaceutical product may be ibrutinib.

Other conversions (of products obtained by the process of the invention either directly or of further products resulting from downstream steps e.g. as may be described herein) may be performed in accordance with standard techniques and steps in the prior art, for instance, amide-forming reactions (in this instance, possible conditions and coupling reagents will be known to those skilled in the art), esterifications, nucleophilic substitutions reactions and aromatic nucleophilic substitution reactions.

There is then further provided a process for the preparation of a pharmaceutical formulation comprising ibrutinib, which process comprises bringing into association ibrutinib (or a pharmaceutically acceptable salt thereof), which is prepared in accordance with the processes described hereinbefore, with (a) pharmaceutically acceptable excipient(s), adjuvant(s), diluents(s) and/or carrier(s).

In general, the processes described herein, may have the advantage that the compounds prepared may be produced in a manner that utilises fewer reagents and/or solvents, and/or requires fewer reaction steps (e.g. distinct/separate reaction steps) compared to processes disclosed in the prior art.

The process of the invention may also have the advantage that the compound(s) prepared is/are produced in higher yield, in higher purity, in higher selectivity (e.g. higher regioselectivity), in less time, in a more convenient (i.e. easy to handle) form, from more convenient (i.e. easy to handle) precursors, at a lower cost and/or with less usage and/or wastage of materials (including reagents and solvents) compared to the procedures disclosed in the prior art. Furthermore, there may be several environmental benefits of the process of the invention.

Examples

The following examples are intended to illustrate the present invention and should not be construed as a limitation of the scope of the present invention.

Preparation of Compounds 6 and 7:

Compound number 5 is prepared in accordance with the general procedures in the scheme below (from Compounds 1, 2, 3 and 4). Thereafter Compound 5 is converted to Compound 6 and 7 under certain conditions:

(i) under the conditions using CuBr as catalyst and DMA as solvent under dry air, Compound 6 is the main product with 10-20% Compound 7 as a side-product. The isolated yield of Compound 6 is ~55.8%.

(ii) under the conditions using $Cu(OAc)_2$ as catalyst and DMSO as solvent under air (that is not dry/dried), Compound 7 is the main product with only trace Compound 6. The isolated yield of Compound 7 is 44.2%.

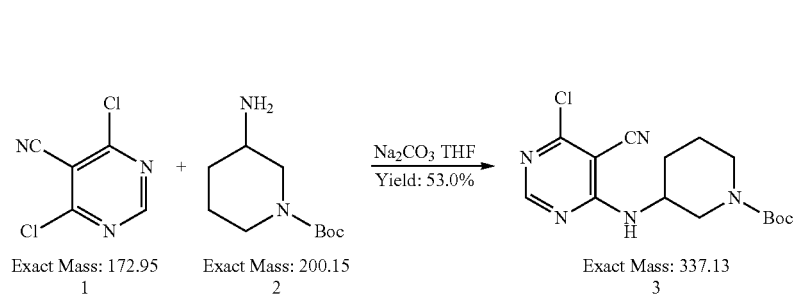
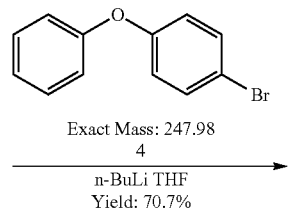
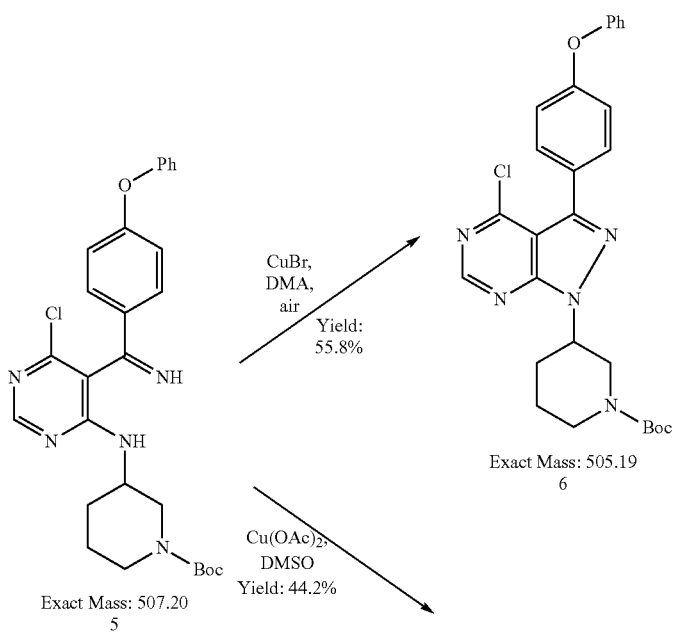
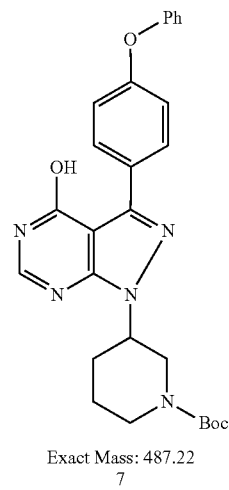
Route from Compound 7 to Compound 11:
This reaction was successful, but low yield due to unstability of Compound 8 The —OH group was activated by reaction with Tf$_2$O (to form the corresponding triflate i.e. Compound 8), which was then substituted in three different ways.

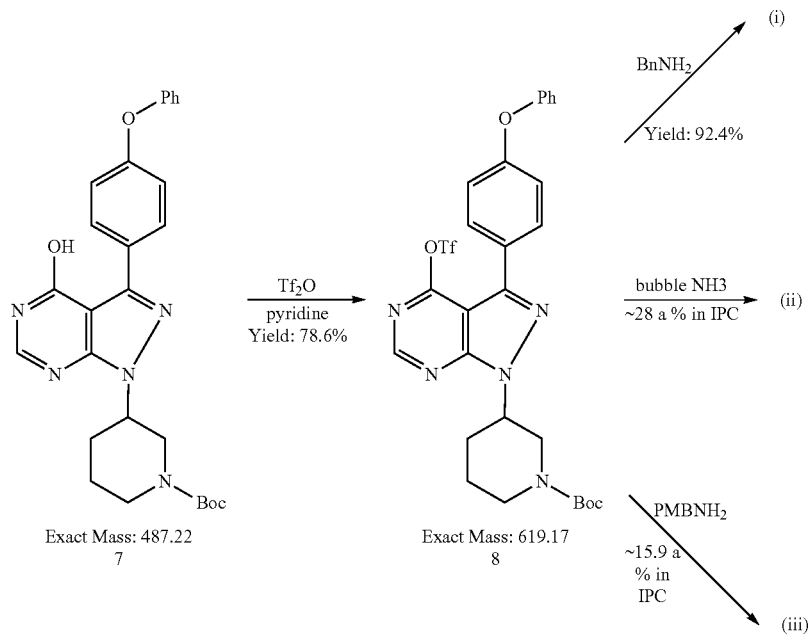

Compound 8 was reacted in three different ways (with three different amines) as indicated above with the amine: (i) NH₂Bn (benzylamine); (ii) NH₃ (ammonia); and (iii) NH₂PMB (4-methoxybenzylamine). These are depicted in the scheme below. The substitution reaction (i) with NH₂Bn was successful, but in the deprotection i.e. "de-Bn" step, the major product was over hydrogenation, and a very low yield of Compound 9 was found. The substitution reactions (ii) and (iii) above with NH₃ and NH₂PMB respectively were successful but did not proceed in very high yield. Hence the low yields to obtain Compounds 10 and 12 from reactions (ii) and (iii).

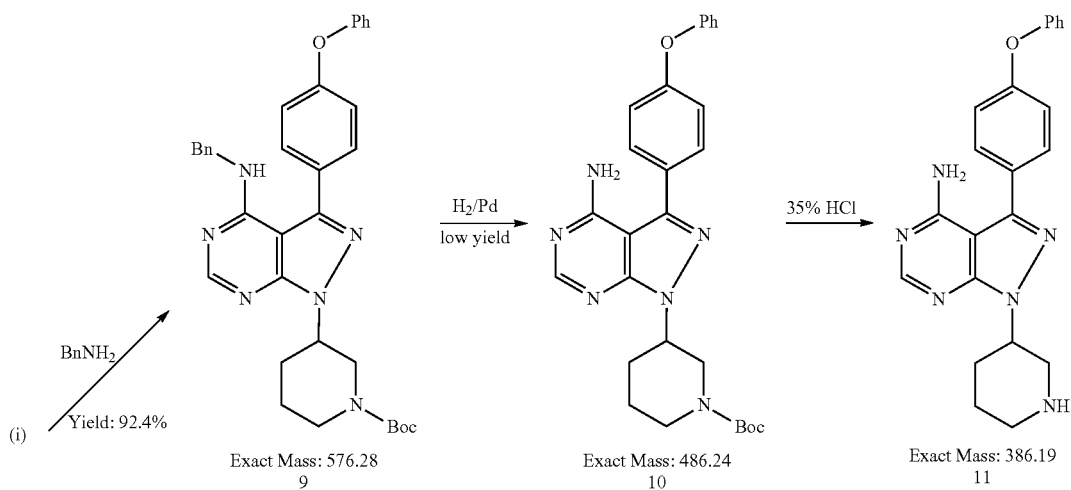

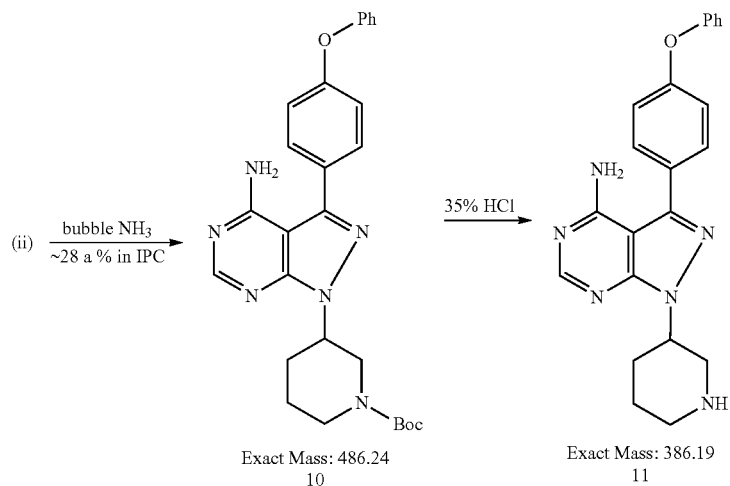

Exact Mass: 486.24
10

Exact Mass: 386.19
11

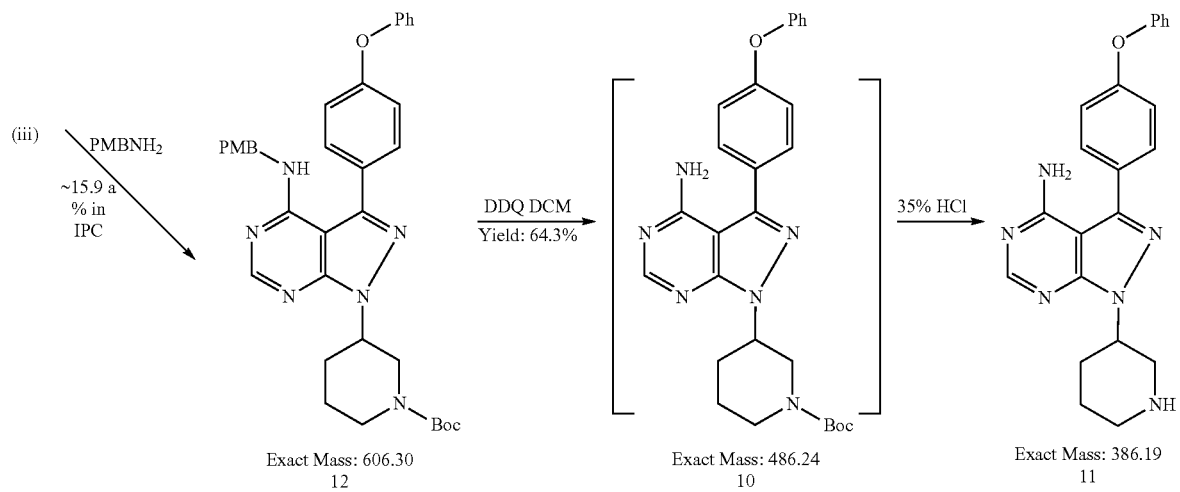

Exact Mass: 606.30
12

Exact Mass: 486.24
10

Exact Mass: 386.19
11

Route from Compound 6 to Compound 11:

There are three routes from Compound 6 to Compound 10, as per the scheme below. The 1st route involves bubbling NH₃ into a solution of Compound 6 in DMA (dimethylacetamide) in the presence of CuBr. Compound 10 was obtained in yield of 92.5%. The 2nd route uses Cu₂O as catalyst, NMP (N-methyl-2-pyrrolidine) as solvent and NH₄OH as reactant. Compound 10 was obtained in yield of 67.2%. The 3rd route involves reaction with PMBNH₂ (4-methoxybenzylamine) to form Compound 12 first and then using DDQ (2,3-dichloro-5,6-dicyano-1,4-benzoquinone) to de-protect the PMB (4-methoxybenzyl) group. Compound 10 was obtained in yield of 57.3% (89.1%*64.2%). From Compound 10 to Compound 11, yield was 73.1%.

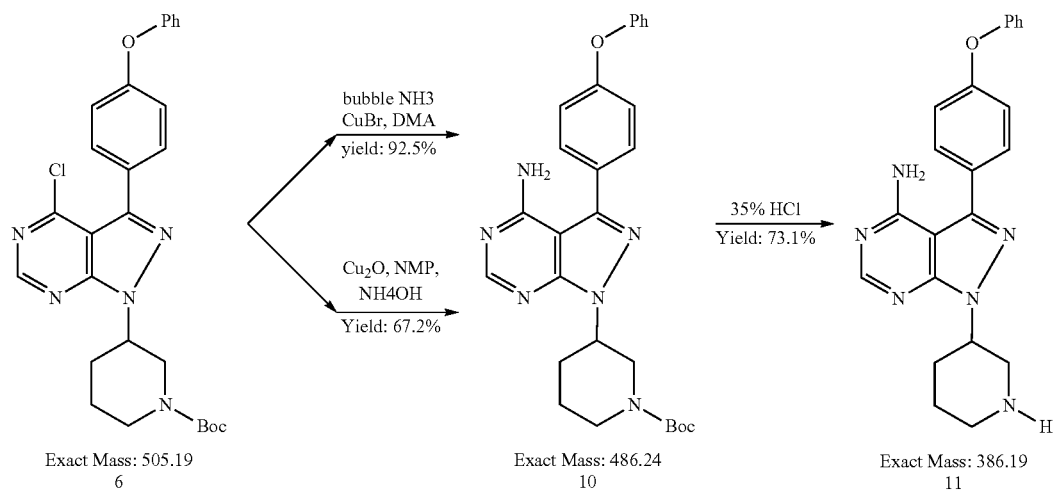
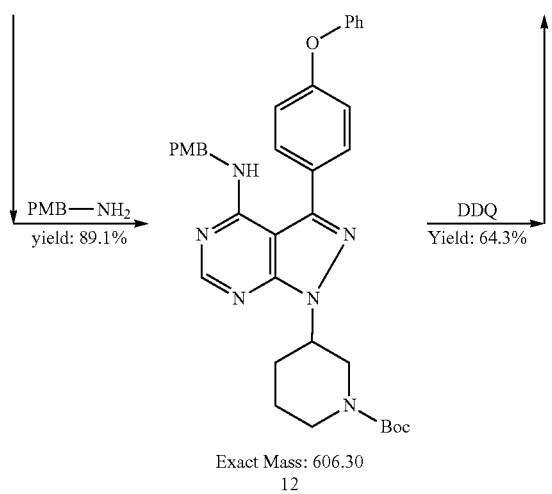
Final Synthesis Route for Compound 11 (Key Intermediate in the Synthesis of Ibrutinib)
This route uses a single (R)-enantiomer of starting material 2 (hereinbelow) labelled as "2R" (where downstream single enantiomers are produced, these are suffixed with "R" compared to the numbering used in schemes above)
-continued
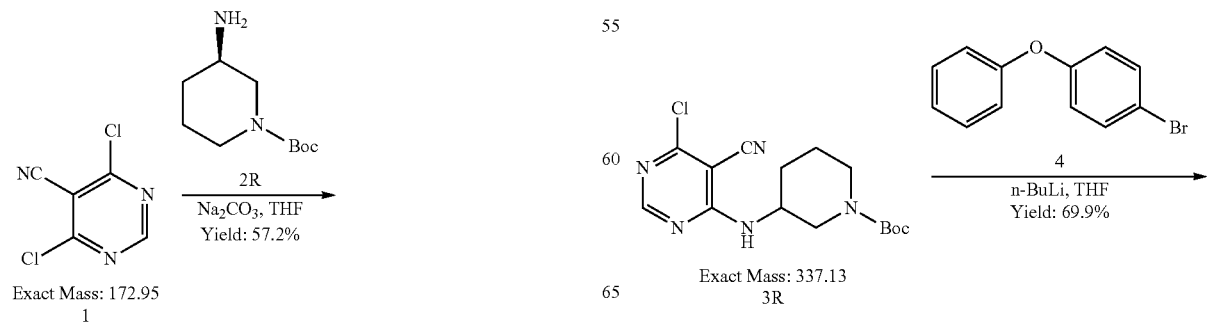

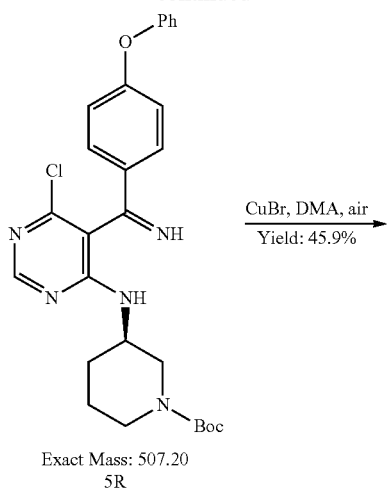

Exact Mass: 507.20
5R

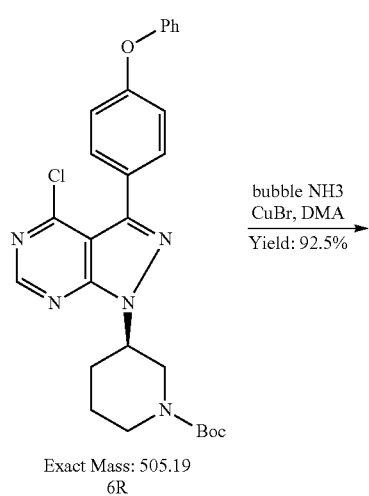

Exact Mass: 505.19
6R

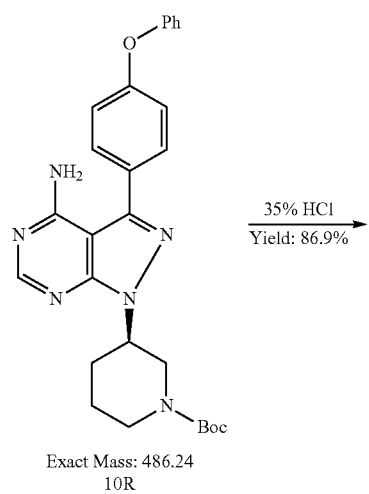

Exact Mass: 486.24
10R

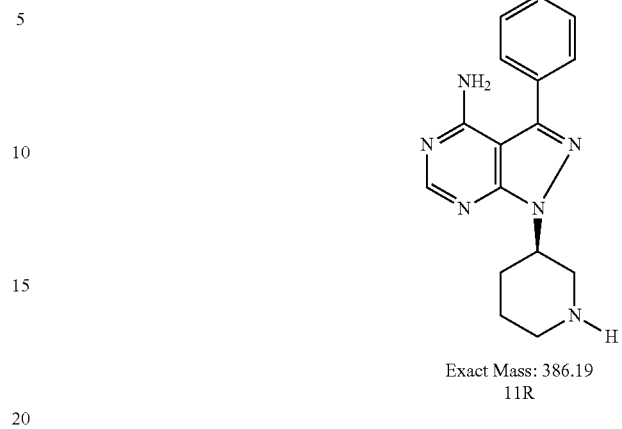

Exact Mass: 386.19
11R

From Compound 1 and Compound 2R to Compound 3R

Experiment Description

Compound 1 (50.01 g, 289 mmol) and Compound 2R (75.24 g, 376 mmol, 1.3 eq.) were dissolved in dry THF (550 mL, 11V) mixed with sodium carbonate (30.6 g, 289 mmol, 1.00 eq). After stirring the mixture at 33° C. under $N_2$ for 24 h, water (500 ml, 10V) was added to quench the reaction and then the phases separated. The organic layer was washed with water (250 ml, 5V) again and the aqueous layer extracted with EA—ethyl acetate (250 ml, 5V) twice. The organic layers were combined and the solvent evaporated under vacuum. The crude product was purified by column chromatography (PE:EA=15:1 to 5:1) to get 55.56 g Compound 3R (35.03 with 99.20% purity and 20.53 g with 98.59% purity) in total yield of 57.19%.

From Compound 3R and Compound 4 to Compound 5R

Experiment Description

Compound 4 (65.03 g, 262 mmol, 3 eq.) was dissolved in dry THF (300 mL, 10V) and then cooled to −70~−75° C. Subsequently, THF solution of n-BuLi (16.73 g, 261 mmol, 3 eq) was added drop-wise into the THF solution of Compound 4 at −70~−75° C. under $N_2$. Compound 3R (29.45 g, 87.4 mmol, 1 eq.) was dissolved in dry THF (300 mL, 10V) and then added drop-wise into the above intermediate solution at −70~−75° C. under $N_2$. After stirring for 1 h, saturated ammonium chloride (300 mL, 10V) was added drop-wise into the reaction mixture to quench the reaction. The solvent was evaporated under vacuum and the crude product was purified by column chromatography (PE:EA=10:1 to 3:1) (petroleum ether/ethyl acetate) to get 30.95 g Compound 5R (2.63 g with 98.21% purity and 28.32 g with 91.51% purity) in total yield of 69.88%.

From Compound 5R to Compound 6R

Experiment Description

Compound 5R (1.05 g, 2.1 mmol), CuBr (148.3 mg, 0.5 eq) and dry DMA (10 ml, 10V) were added into a dry flask, then the reaction mixture was heated to 85° C. and stirred for 10 h under dry air flow. EA (10 ml, 10V) was added into the mixture and the organic layer was washed with water (100 ml, 10V) twice. The solvent was evaporated under vacuum and crude product purified by column chromatography (PE:EA=10:1) to get 0.48 g Compound 6R with 98.61a % HPLC purity in yield of 45.89%.

From Compound 6R to Compound 10R
Experiment Description

Compound 6R (1.72 g, 3.4 mmol) was dissolved into DMA (12 ml, 7V) in autoclave and then NH$_3$ was bubbled for 25 min. CuBr (240 mg, 0.5 eq) was added into the reaction mixture then the mixture heated to 85° C. After stirring for 16 h, EA (26 ml, 15V) was added and the organic layer washed with water (17 ml, 10V) three times. The solvent was evaporated under vacuum and crude product purified by column chromatography (PE:EA=5:1 to 2:1) to get 1.53 g Compound 10R with 99.15a % HPLC purity in yield of 92.5%.

From Compound 10R to Compound 11R
Experiment Description

Compound 10R (1.03 g, 2.1 mmol) was dissolved in toluene (8 ml, 8V) and then water (7.5 ml, 7.5V) was added and then 35% HCl (2.21 g, 21 mmol, 10 eq.), in turn. The reaction mixture was heated to 65° C. and stirred for 2 h. The mixture was cooled to 20-25° C. and then the phases separated. MeOH (5 ml, 5V) was added into the mixture then the pH was adjusted to 10-13 with 30% KOH. The solid was filtered and the cake washed with 50 wt % MeOH/H$_2$O (1 g). The wet cake was dissolved into MeOH (17 ml, 17V) at 45° C. and then 50 wt % KOH/H$_2$O (14 g, 14X) was added drop-wise. The mixture was cooled to 20-25° C. and then the solid filtered and the cake washed with 50 wt % MeOH/H$_2$O (1 g). After drying at 45° C. under vacuum for 16 h, 0.69 g Compound 11R was obtained with 99.7a % HPLC purity and 100% chiral. The yield was 86.9%

From Compound 11R to Ibrutinib

Ibrutinib was prepared in accordance with the procedures disclosed in WO 2016/115356, WO 2008/039218 (Example 1b) and/or WO 2014/139970.

Further Example A: Ibrutinib (or a salt thereof) is prepared by preparing an intermediate using any of the process steps described in Example 1, following by conversion to ibrutinib (or a salt thereof).

Further Example B: A pharmaceutical composition is prepared by first preparing ibrutinib (or a salt thereof) as per Example 2, and then contacting ibrutinib (or a salt thereof) so obtained with a pharmaceutically acceptable carrier, diluent and/or excipient.

The invention claimed is:

1. A process for preparing a compound of formula (I);

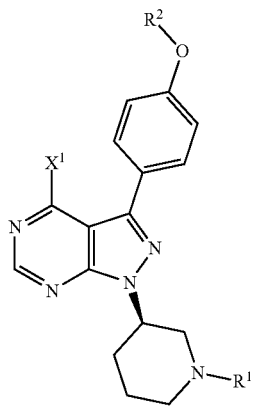

(I)

wherein:
R$^1$ is a nitrogen protecting group;
R$^2$ is hydrogen or aryl;
X$^1$ is a leaving group or —N(R$^3$)R$^4$;
at least one of R$^3$ and R$^4$ is a nitrogen protecting group, and the other is hydrogen or an independent nitrogen protecting group;

wherein the process comprises reacting a compound of formula (II);

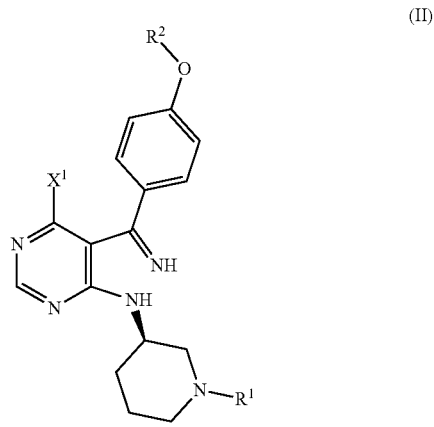

(II)

with an oxidant and a copper-based catalyst.

2. The process of claim 1, wherein the reaction is performed in the presence of a copper-based catalyst and air (O$_2$).

3. The compound of claim 2, wherein the catalyst is Cu(OAc)$_2$ or CuBr.

4. The process of claim 1, wherein:
X$^1$ is halo or —O—Y$^1$; and/or
Y$^1$ is hydrogen; and/or
R$^2$ is phenyl.

5. The process of claim 1, wherein the compound of formula (II) is prepared by reacting a compound of formula (III):

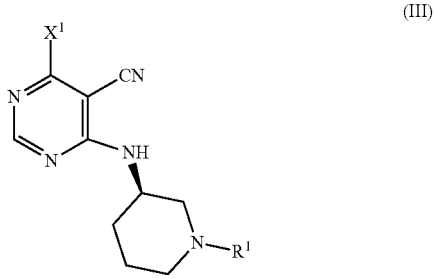

(III)

or a salt thereof, with a compound of formula (IV):

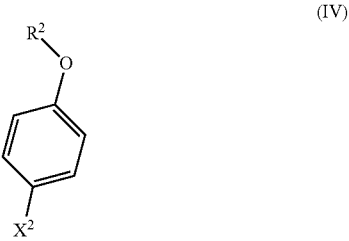

(IV)

or a salt thereof, wherein $X^2$ is a halo, in the presence of an organolithium base.

6. The process of claim 5, wherein the compound of formula (III) is prepared by reacting a compound of formula (V):

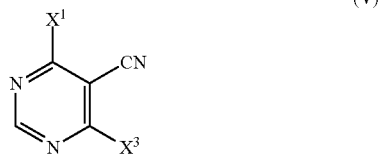
(V)

or a salt thereof, wherein $X^3$ is a suitable leaving group with a compound of formula (VI);

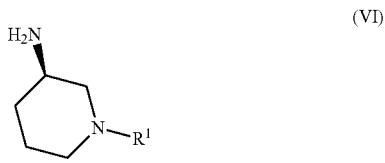
(VI)

or a salt thereof, under nucleophilic aromatic substitution reaction conditions.

7. A process for preparing ibrutinib, comprising reacting the compound of formula (I) prepared according to claim 1 with (i) Cl—C(O)—C(H)=CH$_2$ or (ii) 3-chloropropionyl chloride to form a compound of formula (VII):

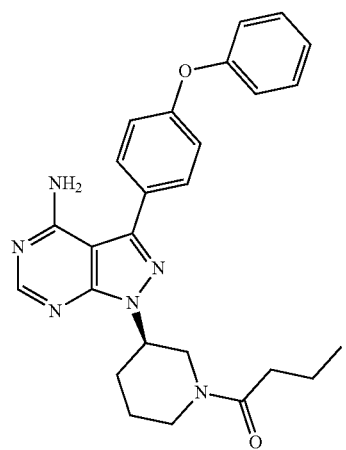
(VII)

or a derivative thereof, and subjecting the compound of formula (VII) to an elimination reaction to provide ibrutinib.

8. A process for preparing a pharmaceutical composition of claim 7, comprising contacting the ibrutinib, or a salt thereof with a pharmaceutically acceptable carrier, diluent and/or excipient.

9. The process of claim 1, wherein $R^2$ is phenyl.

10. The process of claim 1, wherein the leaving group is halo or —O—$Y^1$ and $Y^1$ is hydrogen or a sulfone.

11. The process of claim 10, wherein $X^1$ is tosylate, mesylate, or triflate.

12. The process of claim 1, wherein the sulfone is —S(O)$_2$—$R^x$, wherein $R^x$ is $C_{1-3}$ alkyl optionally substituted by one or more fluoro, or aryl optionally substituted by one or more of halo or $C_{1-3}$ alkyl, wherein the optional substituents are optionally substituted by one or more fluoro.

13. The process of claim 12, wherein $R^x$ is phenyl.

14. The process of claim 1, wherein the oxidant is oxygen.

15. The process of claim 4, wherein $X^1$ is chloro.

16. The process of claim 4, wherein $R^2$ is unsubstituted phenyl.

17. The process of claim 6, wherein the leaving group is halo or O—$Y^2$ and $Y^2$ is a sulfone.

18. The process of claim 17, wherein the leaving group is chloro, bromo or iodo.

19. The process of claim 17, wherein $Y^2$ is —S(O)$_2$—$R^y$, wherein $R^y$ is $C_{1-3}$ alkyl optionally substituted by one or more fluoro, or aryl optionally substituted by one or more of halo and $C_{1-3}$alkyl, wherein the optional substituents are optionally substituted by one or more fluoro.

20. The process of claim 19, wherein the aryl is phenyl.

21. The process of claim 7, wherein compound (VII) is performed in the presence of aqueous NaHCO$_3$ in Me-THF.

22. The process of claim 7, wherein the elimination reaction is performed using 1,8-diazabicyclo(5.4.0)undec-7-ene (DBU).

* * * * *